(12) United States Patent
Wurmfeld et al.

(10) Patent No.: US 12,303,610 B2
(45) Date of Patent: *May 20, 2025

(54) SYSTEM AND METHOD FOR APPLYING ULTRA VIOLET LIGHT DOSES TO CURRENCY BILLS

(71) Applicant: Capital One Services, LLC, McLean, VA (US)

(72) Inventors: David Kelly Wurmfeld, Fairfax, VA (US); Kevin Osborn, Newton Highlands, MA (US)

(73) Assignee: Capital One Services, LLC, McLean, VA (US)

( * ) Notice: Subject to any disclaimer, the term of this patent is extended or adjusted under 35 U.S.C. 154(b) by 48 days.

This patent is subject to a terminal disclaimer.

(21) Appl. No.: 18/356,040

(22) Filed: Jul. 20, 2023

(65) Prior Publication Data
US 2023/0372566 A1 Nov. 23, 2023

Related U.S. Application Data

(63) Continuation of application No. 17/204,529, filed on Mar. 17, 2021, now Pat. No. 11,771,788.

(51) Int. Cl.
A61L 2/24 (2006.01)
A61L 2/10 (2006.01)
(Continued)

(52) U.S. Cl.
CPC ............ A61L 2/24 (2013.01); A61L 2/10 (2013.01); G06K 7/12 (2013.01); G06K 7/1413 (2013.01);
(Continued)

(58) Field of Classification Search
CPC ... A61L 2/04; A61L 2/10; G07F 19/20; G07F 19/201; B65H 5/00; B65H 29/00;
(Continued)

(56) References Cited

U.S. PATENT DOCUMENTS 5,374,814 A 12/1994 Kako et al.
7,353,989 B1 4/2008 Block et al.
(Continued)

FOREIGN PATENT DOCUMENTS

CN 203894795 U 10/2014
CN 204563022 U 8/2015
KR 200478413 Y1 10/2015

Primary Examiner — Jennifer Wecker
Assistant Examiner — Brady C Pilsbury
(74) Attorney, Agent, or Firm — Greenberg Traurig, LLP

(57) ABSTRACT

An apparatus includes a bill feeder, a housing for holding a bill that is received from the bill feeder, sensors coupled to the housing, an ultraviolet (UV) lamp that emits ultraviolet light to illuminate a portion of the bill, a UV shutter to control a power of the ultraviolet light on the bill, a memory and a processor. The processor configured to determine at a property of the bill from a first output of a first sensor, to determine a bill contaminant on the bill from a second output from a second sensor, to retrieve a UV dose rate to be applied by the ultraviolet light needed to sterilize the bill based on the type of bill contaminant on the bill, the property of the bill, an illumination area or any combination thereof, and to apply the UV dose rate to the bill.

20 Claims, 5 Drawing Sheets

(51) Int. Cl.
*G06K 7/12* (2006.01)
*G06K 7/14* (2006.01)
*G07F 19/00* (2006.01)

(52) U.S. Cl.
CPC ......... *G07F 19/202* (2013.01); *A61L 2202/11* (2013.01); *A61L 2202/14* (2013.01)

(58) Field of Classification Search
CPC .... B65H 2701/1824; B65H 2701/1912; G07D 11/10; G07D 11/16; G07D 11/175
See application file for complete search history.

(56) References Cited

U.S. PATENT DOCUMENTS

| | | |
|---|---|---|
| 9,415,124 B2 | 8/2016 | Baek |
| 2003/0030015 A1 | 2/2003 | Waluszko |
| 2008/0087184 A1 | 4/2008 | Kerz |
| 2019/0091738 A1 | 3/2019 | Chen |
| 2021/0308296 A1 | 10/2021 | Cook et al. |
| 2021/0330832 A1* | 10/2021 | Dobbins ................... G07F 9/10 |
| 2021/0366244 A1* | 11/2021 | Denny .................. G07F 19/201 |
| 2022/0257819 A1 | 8/2022 | Pawlowski et al. |

* cited by examiner

SYSTEM AND METHOD FOR APPLYING ULTRA VIOLET LIGHT DOSES TO CURRENCY BILLS

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in drawings that form a part of this document: Copyright, Capital One Services, LLC., All Rights Reserved.

FIELD OF TECHNOLOGY

The present disclosure generally relates to cash disinfection, more particularly to systems for cash disinfection by applying controlled doses of ultraviolet light and methods of disinfection verification thereof.

BACKGROUND OF TECHNOLOGY

Currency bills printed using a linen or a plastic medium may be a transport vector for various viruses and bacteria. The currency bills may transmit viruses, bacteria, and/or other pathogens between people as the currency bills are passed from person-to-person or dispensed from a cash machine to a person, for example. Thus, there is a need in the art for systems and methods for efficiently sterilizing currency bills.

SUMMARY OF DESCRIBED SUBJECT MATTER

In some embodiments, the present disclosure provides an exemplary technically improved apparatus that includes at least the following components of a bill feeder, a housing for holding a bill that is received from the bill feeder, a plurality of sensors, an ultraviolet (UV) lamp that emits ultraviolet light to illuminate a portion of the bill, a UV shutter to control a power of the ultraviolet light on the portion of the bill, a non-transitory computer memory and a processor. The bill feeder may include a bill feed motor that controls a speed that the bill moves in the housing. The plurality of sensors may be coupled to the housing and may be positioned to detect the bill that moves in the housing. The processor may be configured to execute computer code stored in the memory that causes the processor to receive at least one first sensor output from at least one first type sensor from the plurality of sensors, to determine at least one property of the bill based at least in part on the at least one first sensor output, where the at least one property of the bill may identify at least one of:
  (i) a denomination and country of issue of the bill; or
  (ii) a type of material on which the bill is printed;
to receive at least one second sensor output from at least one second type sensor from the plurality of sensors, to determine at least one bill contaminant that is present on the bill based at least in part on the at least one second sensor output, to retrieve from a database a UV dose rate to be applied by the ultraviolet light needed to sterilize the bill based at least in part on:
  (i) the at least bill contaminant on the bill,
  (ii) the at least one property of the bill,
  (iii) an illumination area of the portion, or
  (iv) any combination thereof,
to activate the UV lamp, and to transmit at least one instruction to at least one of the UV shutter or the bill feed motor to result in the UV dose rate to be applied to the bill to sterilize the bill that moves in the housing, the at least one instruction controlling at least one of:
  (i) the UV shutter to vary the power from the UV lamp, or
  (ii) the bill feed motor to control the speed with which the bill moves in the housing.

In some embodiments, the present disclosure provides an exemplary technically improved method that includes at least the following steps of receiving in a housing including a bill feeder, a bill for sterilization, where the bill feeder may include a bill feed motor that controls a speed that the bill moves in the housing. A plurality of sensors may be coupled to the housing and positioned to detect the bill that moves in the housing. At least one first sensor output from at least one first type sensor from the plurality of sensors may be received. At least one property of the bill based at least in part on the at least one first sensor output may be determined. The at least one property of the bill may identify at least one of:
  (i) a denomination and country of issue of the bill; or
  (ii) a type of material on which the bill is printed;
At least one second sensor output from at least one second type sensor from the plurality of sensors may be received. At least one bill contaminant present on the bill based at least in part on the at least one second sensor output may be determined. An ultraviolet (UV) dose rate to be applied to the bill by ultraviolet light needed to sterilize the bill based at least in part on: the at least one bill contaminant present on the bill, the at least one property of the bill, an illumination area of a portion of the bill, or any combination thereof may be retrieved. At least one instruction to at least one of a UV shutter or the bill feed motor to result in the UV dose rate to be applied to the bill to sterilize the bill that moves in the housing may be transmitted, the at least one instruction controlling at least one of:
  (i) a UV shutter to vary a power from the UV lamp, or
  (ii) the bill feed motor to vary the speed that the bill moves in the housing.

BRIEF DESCRIPTION OF THE DRAWINGS

Various embodiments of the present disclosure can be further explained with reference to the attached drawings, wherein like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as limiting, but merely as a representative basis for teaching one skilled in the art to variously employ one or more illustrative embodiments.

DETAILED DESCRIPTION

Figure 1:
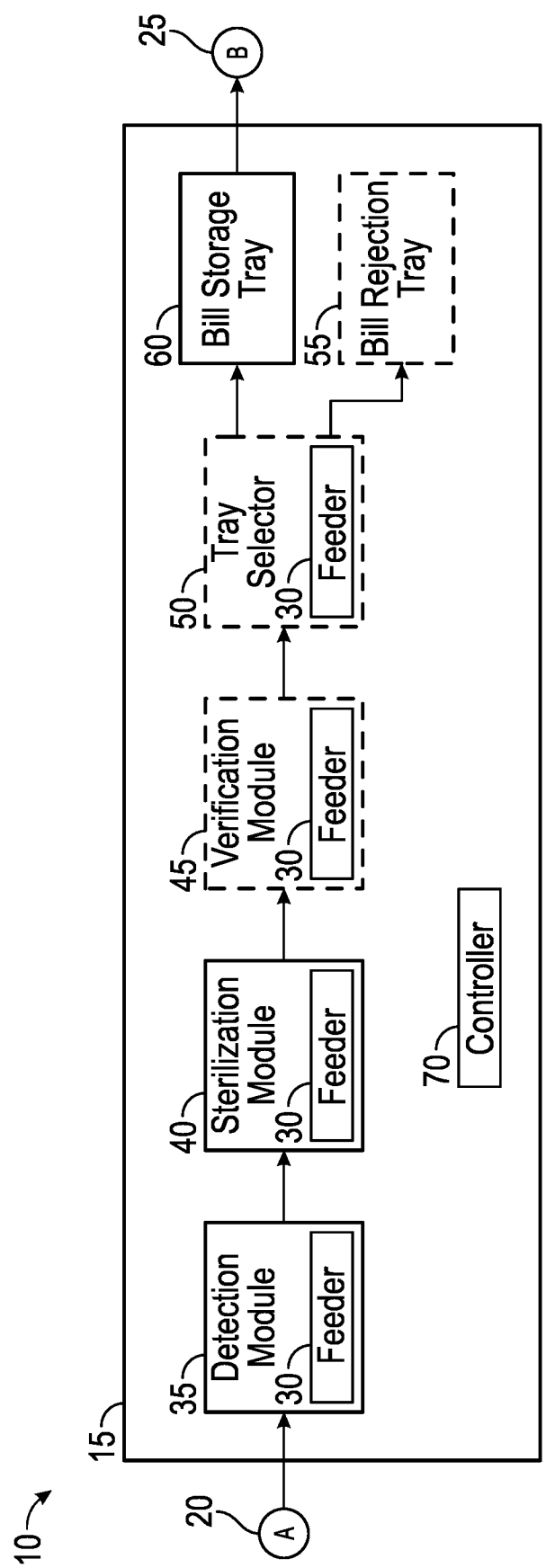
FIG. 1 is a functional block diagram of a bill sterilization apparatus in accordance with one or more embodiments of the present disclosure.

Various detailed embodiments of the present disclosure, taken in conjunction with the accompanying figures, are disclosed herein; however, it is to be understood that the disclosed embodiments are merely illustrative. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation can be used in guiding the physical process.

As used herein, the term "dynamically" and term "automatically," and their logical and/or linguistic relatives and/or derivatives, mean that certain events and/or actions can be triggered and/or occur without any human intervention. In some embodiments, events and/or actions in accordance with the present disclosure can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

As used herein, the term "runtime" corresponds to any behavior that is dynamically determined during an execution of a software application or at least a portion of software application.

Embodiments of the present disclosure herein describe systems and methods for sterilizing currency bills that are quick and safe. A bill sterilization apparatus may include a plurality of sensors coupled to a housing that is configured to sterilize a currency bill with ultraviolet light. The bill sterilization apparatus may identify at least one property of the bill (e.g., currency denomination, country, material that the currency bill is printed on, ink type), and at least one bill contaminant that is present on the bill. The bill contaminant typically changes the UV dose rate needed to sterilize the bill.

In some embodiments, the bill sterilization apparatus 10 may obtain the proper UV dose rate from a database based on these parameters. The UV light may illuminate the currency bills within an illumination area and apply the proper UV dose rate to the currency bill so as to properly sterilize the bill and disinfect the bill. The proper UV dose rate may be applied to the bill by controlling the UV power applied to the bill within the illumination area and/or by controlling the speed of the bill moving within the illumination area.

FIG. 1 is a functional block diagram of a bill sterilization apparatus 10 in accordance with one or more embodiments of the present disclosure. The bill sterilization apparatus 10 may include a housing 15 that further includes a bill detection module 35, a sterilization module 40, a verification module 45, a tray selector 50 that may route currency bills into a bill storage tray 60 or a bill rejection tray 55. A bill feeder 30 may include a bill feed motor that moves the currency bill inserted into the bill sterilization apparatus 10 at a port A 20 and into the bill storage tray 60 or the bill rejection tray 55 as shown in FIG. 1. The bill feeder 30 is shown as a block common between the modules shown in FIG. 1 because the bill feeder 30 should propel the bills from module to module with a same speed to prevent bill jams. A controller 70 may control the functionality in the bill sterilization apparatus 10 as described herein.

In some embodiments, the bill sterilization apparatus 10 or any modules thereof may be integrated into a cash machine (e.g. automatic teller machine, cash recycler), for example. In the exemplary embodiment shown in FIG. 1, a user may enter the unsterilized bills into a slot in the cash machine and/or a bank employee may load the cash machine with bills. The deposited and/or loaded bills into the cash machine may have viruses, bacteria and/or other pathogens attached to the bills. The unsterilized bills may first pass through port A 20 of the bill sterilization apparatus 10 to be sterilized. The sterilized bills may exit at port B 25 to be stored in a regular manner within the cash machine.

In some embodiments, the port B 25 may be placed at any suitable location in the bill sterilization apparatus 10. For example, the bill sterilization apparatus 10 may include the detection module 35 and the sterilization module 40. The tray selector 50, the bill storage tray 60 and the bill rejection tray 55 may be part of the cash machine itself where bills are not accepted into the cash machine unless sterilized.

Figure 2:
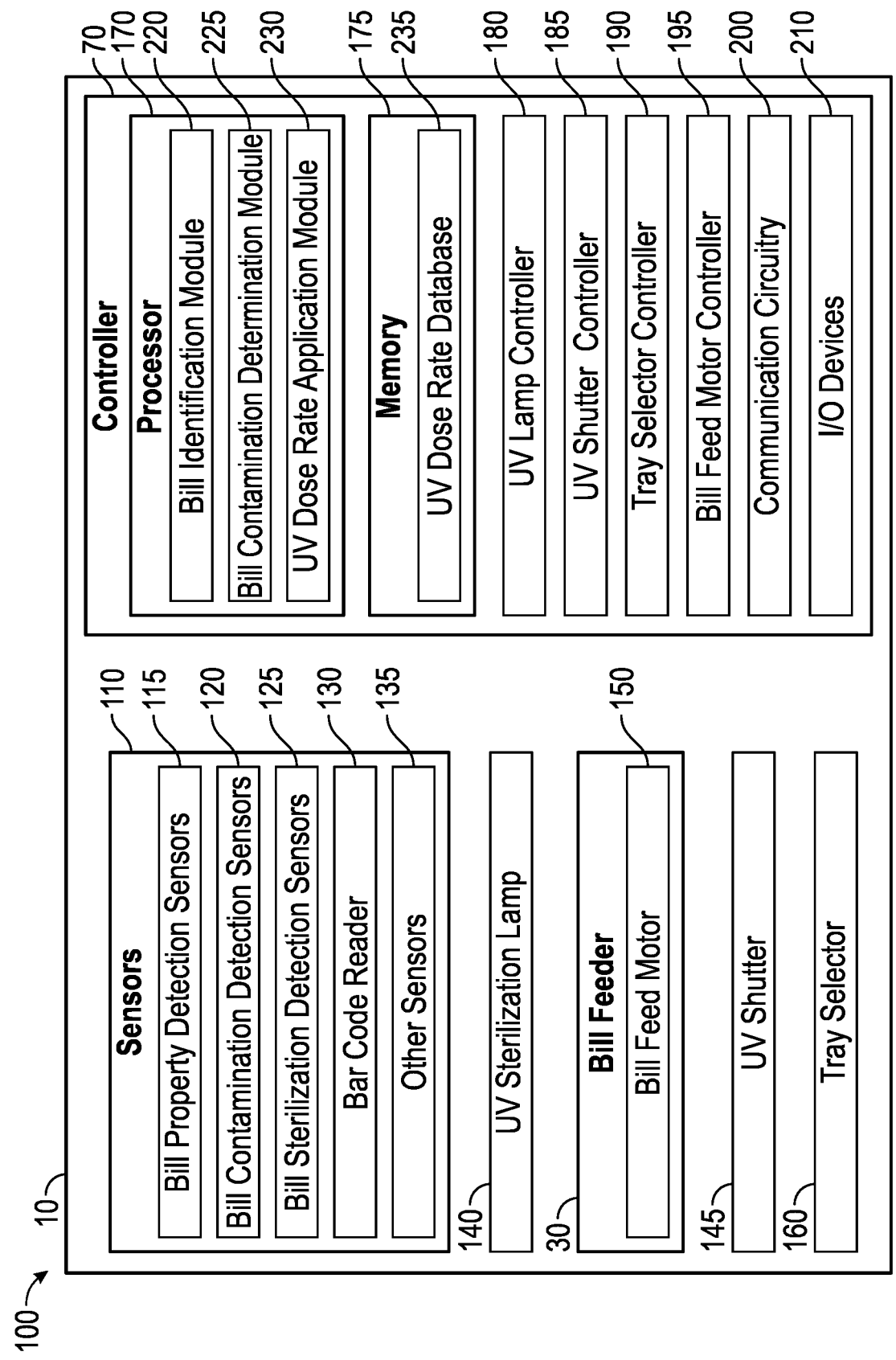
FIG. 2 is a block diagram of a bill sterilization apparatus in accordance with one or more embodiments of the present disclosure.

FIG. 2 is a block diagram 100 of a bill sterilization apparatus 10 in accordance with one or more embodiments of the present disclosure. The bill sterilization apparatus 10 may include a plurality of sensors 110, a UV sterilization lamp 140, the bill feeder 30 driven by a bill feed motor 150, a UV shutter 145 for controlling the UV light intensity incident on the bill, a tray selector 160, and a controller 70.

In some embodiments, the controller 70 may implement a proportional-integral-derivative (PID) control mechanism for sterilizing the bills.

In some embodiments, the plurality of sensors 110 may be coupled and/or affixed to the housing 15 of the bill sterilization apparatus 10. The plurality of sensors 110 may include bill property detection sensors 115, bill contamination detection sensors 120, bill sterilization detection sensors 125, a barcode reader 130, and other sensors 135.

In some embodiments, the controller 70 may include a processor 170, a non-transitory computer memory 175, a UV lamp controller 180, a UV shutter controller 185, a tray selector controller 190, a bill feed motor controller 195, input and output (I/O) devices 210, and communication circuitry 200 for enabling the bill sterilization apparatus 10 to communicate over any suitable wired and/or wireless communication network. The UV lamp controller 180 may be used to activate the UV sterilization lamp 140.

In some embodiments, the processor 170 may execute software modules stored in the memory 175 that sends instructions to each of the elements of the bill sterilization apparatus 10 to perform the functions as described herein. The software modules may include a bill identification module 220, a bill contamination determination module 225, and a UV Dose Rate Application Module 230.

In some embodiments, the bill identification module 220 may be configured to receive output data from the bill property detection sensors and determine at least one property of the bill such as a denomination, country of issue, and/or a type of material on which the bill is printed.

In some embodiments, the bill contamination determination module 225 may use output data from the bill contamination detection sensors 120 to determine at least one bill contaminant that is present on the bill.

In some embodiments, the UV Dose Rate Application Module 230 may use the at least one property of the bill and/or the at least one bill contaminant on the bill in querying a UV Dose Rate Database 235 stored in the memory 175. In other embodiments, the UV Dose Rate Database 235 may be stored in a remote electronic resource in communication with the communication circuitry 200 over a communication network.

In some embodiments, the UV Dose Rate Database 235 may be a lookup table that provides a specific UV Dose Rate for the specific at least one property of the bill and/or the at least one bill contaminant present on the bill (e.g., a specific UV dose rate tailored to a specific bill). The UV Dose Rate Application Module 230 may relay this data to the UV Lamp Controller 180, the UV Shutter Controller 185, and/or the Bill Feed Motor Controller 195 of the sterilization module 40 so as to apply the specific UV Dose Rate to the bill.

In a first exemplary embodiment, the bill sterilization apparatus 10 may use the detection module 35 to receive the bill to be sterilized and to detect the at least one property of the bill and/or the at least one bill contaminant that is present on the bill. The bill may then be fed into the sterilization module 40 by the bill feeder 30. The sterilization module 40 may control the UV power from the UV sterilization lamp 140 using a UV shutter 145 illuminating a portion of the bill. The sterilization module 40 may control the bill feed motor 150 in the bill feeder 30 so as to vary the speed of the bill through the sterilization module 40. This controls the exposure time in which the UV light illuminates the portion of the bill. The sterilized bill may be then routed by the feeder into the bill storage tray 60 or into any section of a cash machine, for example.

In a second exemplary embodiment, the bill sterilization apparatus 10 in addition to the elements of the first exemplary embodiment may also include a verification module 45 (elements shown in dotted line boxes) to verify if the specific UV Dose Rate applied to the bill succeeded to sterilize the bill. If the verification module 45 verifies that the bill was sterilized in the sterilization module 40 in accordance with the specific UV dose rate, the bill may be routed by the tray selector 50 into the bill storage tray 60. If the verification module 45 assesses that the bill was not adequately sterilized, the bill may be routed by the tray selector 50 into the bill rejection tray 55.

Figure 3:
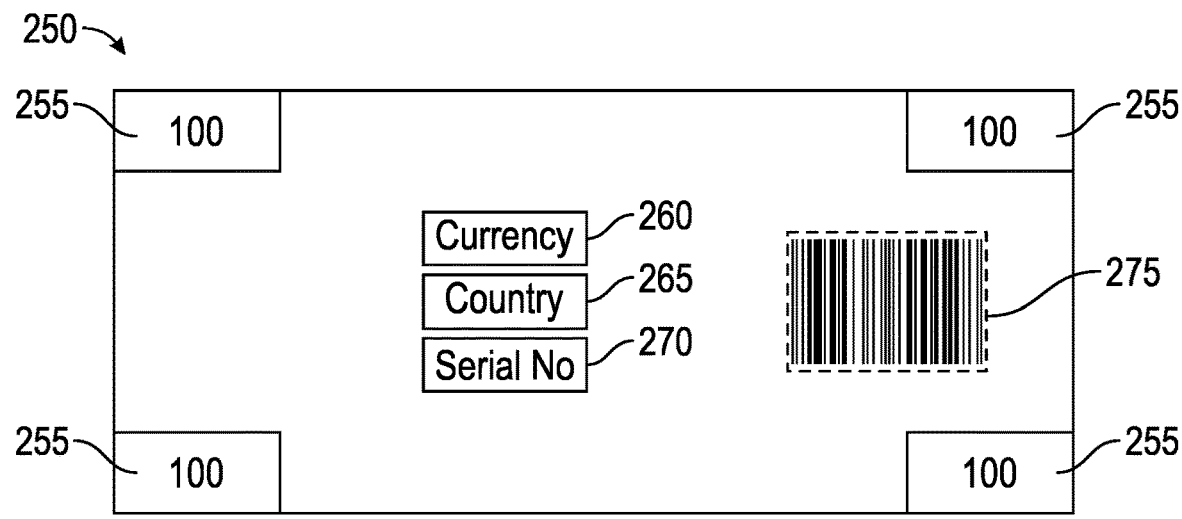
FIG. 3 is a diagram of a currency bill in accordance with one or more embodiments of the present disclosure.

FIG. 3 is a diagram of a currency bill 250 in accordance with one or more embodiments of the present disclosure. The currency bill 250 may include the following indicia: denomination 255 such as "100" currency units, a currency 260 (e.g., U.S. dollar, Euro), a country 265, and a serial number 270. In some embodiments, the currency bill 250 may include a barcode 275 that may be printed using UV sensitive opaque inks that changes color from white to another color after being exposed to a predefined dosage of UV light. As a result, the barcode 275 may be used to verify that the currency bill 250 was properly sterilized according to the specific UV Dose Rate for the at least one property of the specific bill and/or the at least one bill contaminant that is present on the specific bill.

Figure 4A:
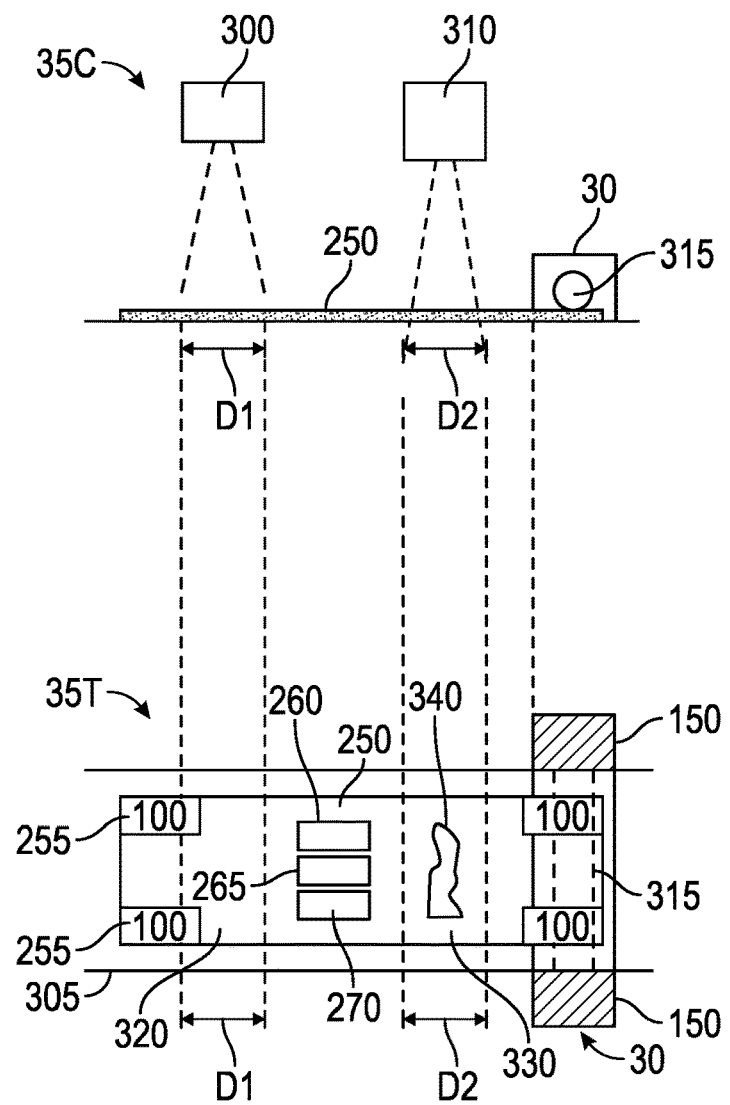
FIG. 4A illustrates a side view and a top view of a bill detection module in accordance with one or more embodiments of the present disclosure.

FIG. 4A illustrates a side view 35C and a top view 35T of the bill detection module 35 in accordance with one or more embodiments of the present disclosure. The bill detection module 35 may include a bill 250 that may be held between guides 305 as the bill 250 moves through the module with the bill feeder 30.

In some embodiments, the bill feeder 30 may include, but is not limited to a roller 315 contacts the bill 250 as it rotates to propel the bill forward. The rotation of the roller 315 may be controlled by bill feed motors 150 which may be subsequently controlled by the bill feed motor controller 195. However, any suitable bill feed mechanism may be used for moving the bill 250 along the bill detection module 35 at a predefined speed and the bill feed mechanism is not limited to the roller 315 contacting the bill 250 while rotating as shown in FIG. 4A.

In some embodiments, the bill detection module 35 may include at least one first sensor 300 for detecting at least one property of the currency bill 250 such as the denomination 255, the currency 260, the country 265 and/or the Serial No. 270, for example. The at least one first type sensor 300 may detect different properties of the currency bill 250 within a lateral distance $D_1$ as the currency bill 250 moves under the at least one first type sensor 300.

In some embodiments, the bill 250 may include security features such as, for example, security inks, magnetic inks, embedded security threads, watermarks, Intaglio printing, see-through registers, special foil, special foil elements, iridescent stripes and shifting colors. These security features may be used to encode the properties of the currency bill 250 in a proprietary manner, such as the denomination 255, the currency 260, the country 265 and/or the Serial No. 270, for example.

In some embodiments, the at least one first type sensor 300 may be a plurality of different sensor types each configured for detecting the each of the different security features and the proprietary property information encoded therein. For example, the at least one first type sensor 300 may include solid state sensors, optically-tuned, light dependent resistor (LDR) light resistors, photoresistors, reflectometers, and/or densitometers (e.g., to detect opacity and how dense is the bill).

In some embodiments, the first type sensor 300 may be a magnetic sensor, for example, configured to detect the magnetic inks, which are paramagnetic and may have iron filings. The magnetic sensor may generate a magnetic field for detecting a magnetic signature of the currency bill 250 which is typically indicative of the denomination 255.

In some embodiments, the first type sensor 300 may be a visual detector for detecting a beginning and an end of the currency bill for determining the length of the bill. For example, each Euro bill has a different length based on the denomination 255 so determination of the length of the bill may be enough to assess the denomination 255 and other properties of the bill.

In some embodiments, in the same vein, embedded threads in the currency bill 250 may glow (e.g., fluoresce) when exposed to different wavelengths of light, such as embedded threads in linen, for example. Hence, the at least one first type sensor may illuminate the currency bill 250 with different wavelengths of light within a lateral distance $D_1$ as the currency bill 250 moves under the at least one first type sensor 300 and to detect fluorescence of emitted light which may be indicative of the denomination 255, the currency 260, and/or the country 265.

In some embodiments, the Bill Identification Module 220 may determine the at least one property of the currency bill 250 (e.g., the denomination 255, the currency 260, the country 265 and/or the Serial no. 270, from the output data of the at least one first type sensor 300. The at least one property of the currency bill 250 may be indicative of the physical properties of the currency bill 250, such as the thickness, the opacity, the material on which the bill is printed on (e.g., plastic polymers, mylar, cotton, linen, paper). This information may be very important in determining the UV dose rate.

In some embodiments, the bill detection module 35 may include at least one second type sensor 310 for detecting at least one bill contaminant 340 within a lateral distance $D_2$ as the currency bill 250 moves under the at least one second type sensor 310. The at least one bill contaminant 340 as shown on the currency bill 250 may include, for example, humidity, grease, skin oils, hand cream, glitter, and powder. These bill contaminants may change the UV Dose Rate needed for bill sterilization if dependent only on the at least one property of the bill. For example, grease on the bill may change the optical opaqueness of the bill, so as to have a different reflective signature without grease. This may be detected by using a phototransistor to measure the density, relative density, and/or the relative reflection of the bill, and/or by using a densitometer to measure how much light goes through the bill.

In some embodiments, the Bill Contamination Determination Module 225 may use the output data from the at least one second type sensor 310 to determine the contaminants 340 on the currency bill 250. For example, the at least one second type sensor 310 may be a reflectometer to detect surface contaminants.

In some embodiments, UV Dose Rate Application Module 230 may query the UV Dose Rate Database 235 for determining the optimal UV dose rate based on the at least one property and/or the at least one bill contaminant 340 of the currency bill 250. Applying the correct UV dose rate to sterilize the bill is critical. If the UV dose rate is too high, the material of the bill may disintegrate or even burn, currency bills printed on mylar may distort, and/or the inks used to print the indicia on the currency bill 250 may fade. Conversely, if the UV dose rate is too low, the bill may not be adequately sterilized.

In some embodiments, the sensors in the detection module 35 may be include a camera (e.g., still or video camera) to detect the at least one property of the bill and/or the at least of bill contaminant on the bill by applying image processing/recognition techniques to the captured images by the camera.

In the context of the present disclosure, the term UV dose may also be referred to as the fluence. The UV dose may have units of $mJ/cm^2$. The UV dose rate may be in units of $mJ/cm^2$-s, for example.

In some embodiments, any number of detectors (not shown) that are sensitive to wavelengths in any suitable wavelength range may be used to detect the translucence of the bill by illumination generated by the first type sensor by 300 and/or by the second type sensor 310 on one side of the currency bill 250 and the transmitted light through the bill may be detected on the backside of the currency bill 250 substantially opposite to the first type sensor by 300 and/or by the second type sensor 310 to measure the translucence of the currency bill 250.

Figure 4C:
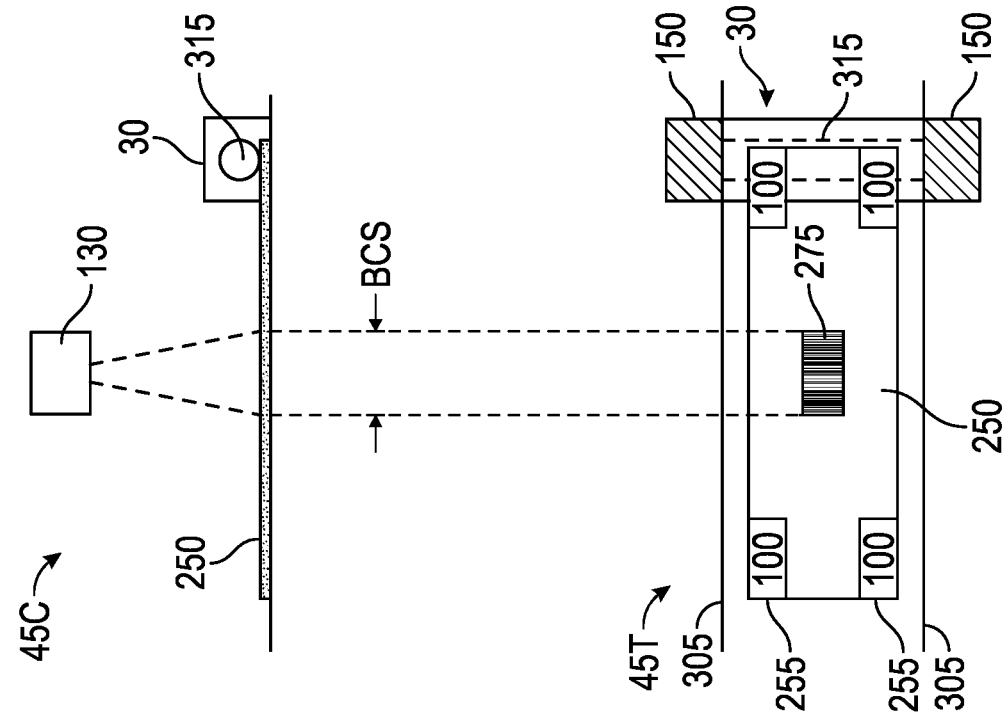
FIG. 4C illustrates a side view and a top view of a bill sterilization verification module in accordance with one or more embodiments of the present disclosure.
Figure 4B:
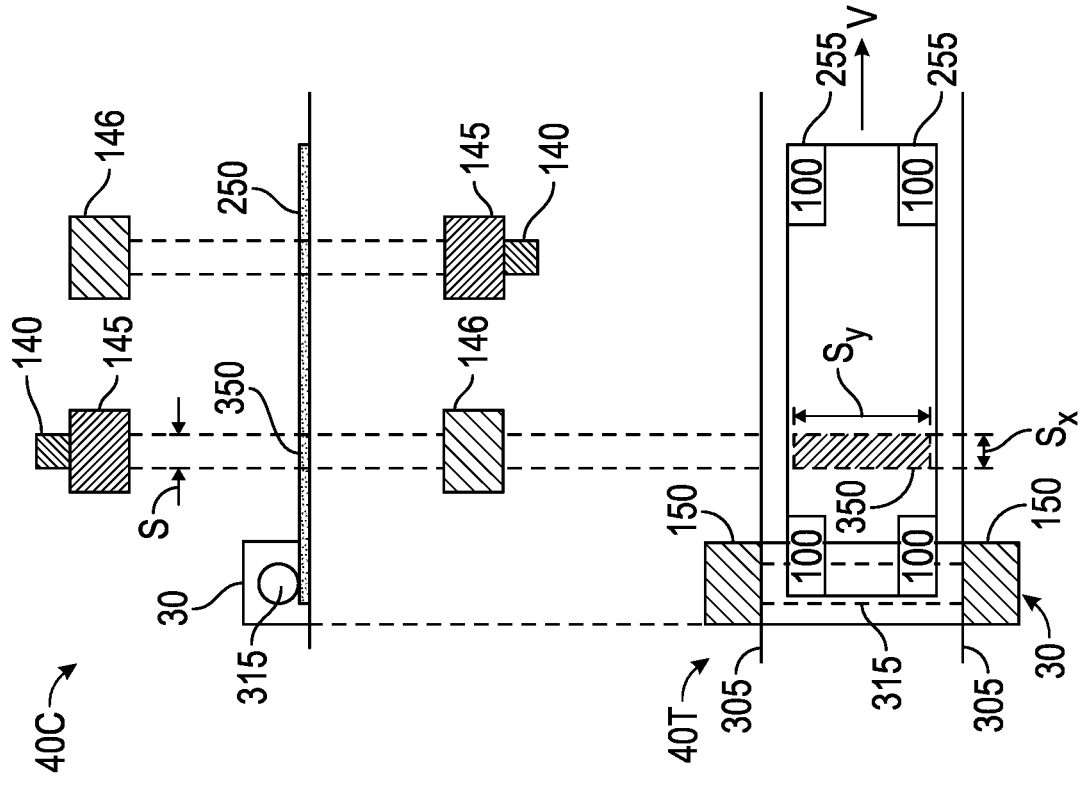
FIG. 4B illustrates a side view and a top view of a bill sterilization module in accordance with one or more embodiments of the present disclosure.

FIG. 4B illustrates a side view 40C and a top view 40T of the bill sterilization module 40 in accordance with one or more embodiments of the present disclosure. The bill sterilization module 40 may include the bill 250 that may be held between the guides 305 as the bill 250 moves through the module by the bill feeder 30. A UV lamp 140 may be used as the UV light source for generating the UV light. A UV shutter 145 may be used to control the sterilization power illuminating a portion 350 of the currency bill. A UV detector 146 may be placed on the bottom side of the bill to measure any UV light penetrating the currency bill 250. The portion 350 for sterilizing the bill 250 may have linear dimensions of $S_x$ and $S_y$ as shown in FIG. 4B. Thus, the illuminated area on the currency bill 250 may be given by $S_x * S_y$. In some embodiments, a UV monitor sensor (not shown) may be used with the UV lamp 140 and the UV shutter 145 to monitor the UV dose.

In some embodiments, the UV shutter 145 may be a mechanical shutter to provide coarse on-off exposure of the currency bill 250 from the UV lamp 140.

In some embodiments, far UV (UVC) light with a wavelength range of 100 nm-290 nm, and particularly a UVC wavelength of 222 nm, for example, may be used to effectively kill viral pathogens such as COVID-19 and SARS-CoV-2. UVC light in a wavelength range of 260-265 nm is the most effective germicidal wavelength range in which DNA absorbs the highest levels of UV light for killing the broadest range of bacterial and/or viral pathogens. UVC light may be used to sanitize currency bills with a fluence of about 2 $mJ/cm^2$ of UVC light as described herein.

In some embodiments, due to the short penetration depth of the UVC light with skin depths on the order of 40-70 Å, UV illumination from both sides of the currency bill 250 may be used for sterilization as shown in FIG. 4B where UV lamps 140 and UV detectors 146 may be placed on both sides of the currency bill 250. The UV detectors 146 may be used to detect the condition of the bill. Note that for a dirty bill with contaminants on the bill (e.g., hand cream, dust, glitter), a longer exposure of UV light for sterilization may be needed.

In some embodiments, since the sterilization module 40 is typically within a closed system, these latter UV wavelengths (UVA and UVB) may be used to sterilize the bills so long as overexposure or bill jams in the machines do not damage the bills or cause the bills to burn. However, the UVA and/or UVB exposure profiles from UVA/UVB lamps may not be deterministic thus impacting reliability within the bill sterilization apparatus 10. In contrast, the UVC lamps are stable and reliable.

In some embodiments, different wavelengths may be applied to be able to penetrate the bill with different opacities based on the individual exposure profile (UV dose rate) based on the properties of the specific bill. For example, wavelengths in the microwave spectrum, or the IR spectrum may be efficacious for sterilizing the currency bill 250.

In some embodiments, once the UV Dose Rate Application Module 230 determines the UV Dose Rate for the specific currency bill to be sterilized based on the at least one property and the at least one bill contaminant that is present on the specific currency bill, the UV Dose Rate Application Module 230 may apply the UV Dose Rate to the bill to be sterilized through: (i) the UV Lamp controller 180 to control the UV power level from the UV Sterilization Lamp 140 incident on the UV shutter 145; (ii) the UV Shutter Controller 185 to control the UV power level from the output of the UV Shutter 145 incident on the portion 350 of the illuminated region on the currency bill 250; and/or (iii) the Bill Feed Motor Controller to control the bill feed motor 150 to vary the speed of the currency bill 250, or more specifically the linear speed of the portion 350 through the illuminated area in shown in FIG. 4B in the direction of a vector v (velocity).

However, out of practical considerations, some UVC lamps may operate with a fixed output power so it may be easier to implement UVC power control using the UVC shutter. Furthermore, the cash machine is a complex electromechanical system. When the detection module 35 and/or the sterilization module 40 may be used in the cash machine, for example, it may be advantageous not to vary the speed of the bill within the system, but to match the speed v of the bill to that of any bill feed mechanisms within the cash machine.

In some embodiments, the detection sensors and the sterilization module 40 when integrated into a cash machine may be placed anywhere in the path of the bill traversing the components of the cash machine such that no bills may enter the main components of the cash machine unless they traverse the sterilization module 40.

In some embodiments, the UV lamp 140 may be, for example, UV lamps such as Krypton-11 or Krypton-36 from Far UV Technologies, Inc (Far UV Technologies, Inc., 7208 Wornall Rd, Suite 210, Kansas City, MO 64114). Similarly, UV lamps may be UVC light emitting diode chips (see for example, Shenzen Guangmai Electronics Co, Ltd.) In some embodiments, the UV shutter 145 may be a liquid crystal shutter, which may toggle between a clear state and an opaque state as controlled by the UV shutter controller 185 (see for example, liquid crystal shutters from Liquid Crystal Technologies, 24300 Solon Road, Suite 100, Cleveland, Ohio 44146).

In some embodiments, the UV lamp 140 may be an array of a plurality of UVC light emitting diode chips, an array of a plurality of UVC laser diodes. The current-controlled UV light frequency emitted from these devices may be controlled by the UV Lamp Controller 180, such as by controlling the current. The UV Lamp Controller 180 may control the power emitted by these arrays simply by switching any number of LEDs and/or UVC laser diodes on and off in any suitable configuration to control the UV exposure on the currency bill 250.

In some embodiments, if the currency bills are not very UV translucent, other wavelengths may be used to measure the condition of the bill contaminants and the UV sterilization exposure may be increased accordingly (e.g., UV exposure time and/or intensity).

In some embodiments, pulse width modulation (PWM) control may be applied by the UV Lamp Controller 180 to the UV Lamp 140, the UVC LED array, the UVC laser diode array, or any combination thereof to control the UV light illumination emitted from these devices.

When an object and/or a surface and/or any physical area such as a room may be sterilized from viral and/or bacterial pathogens, such as a COVID-19, for example, by the use of UV lamps, it may be difficult to verify whether enough UV exposure was administered to sterilize the object and/or the surface and/or the area. For example, the wrong wavelength of light, or too little exposure time, may only partially destroy the pathogens. Furthermore, there may be legal implications in declaring that an area is clean from pathogens, for example, when it is not in reality.

In some embodiments, UV sensitive inks may be used to create a barcode tag. The barcode (e.g., a standard barcode or QR code) may be printed on any suitable substrate and may include location information, for example.

In some embodiments, the UV sensitive ink may be invisible before sterilization. However, the UV sensitive ink may become visible after receiving a predefined level of exposure to a UV dose. Thus, a barcode reader may be used to read the barcode tags now visible that may be placed at any location to verify that the locations have been sterilized using UV sterilization, so as to log that a specific area has been properly exposed and cleaned from pathogens.

In some embodiments, the UV sensitive inks used to print the barcode may include photochromic dyes that have no color until exposed to UV light such as polyoxometalate based inks. In some embodiments, the photochromic process in the UV sensitive inks may be irreversible or reversible, such that after removal from the UV light, the barcode may disappear.

FIG. 4C illustrates a side view 45C and a top view 45T of the bill sterilization verification module 45 in accordance with one or more embodiments of the present disclosure. In the same vein, UV sensitive inks may be used to print the barcode 275 on the currency bill 250 that is invisible before UV exposure and becomes visible after UV exposure. The bill 250 with the barcode 275 may exit the sterilization module 40 into the verification module 45.

In some embodiments, the barcode 275 may be printed on the currency bill 250 using a photochromic ink such that the barcode 275 becomes visible using a UV dose required for sterilization that exceeds the UV dose required to cause the barcode 275 to become visible. This may be used to indicate that the currency bill 250 was sterilized in accordance with the UV dose rate received from the UV Dose Rate Database 235.

In some embodiments, when the currency bill 250 is properly sterilized with the correct UV dose rate and the barcode 275 becomes visible, the bill sterilization may be verified by using a barcode reader 130 to read the visible barcode 275 on the currency bill 250. The speed v of the bill as determined by the bill feeder and the rotation speed of the roller 315 is configured to ensure that the barcode scan (BCS) rate of the barcode reader 130 is fast enough to capture the barcode 275 as it moves under the barcode reader 130.

In some embodiments, where the barcode 275 may not be used for sterilization verification, the processor 170 may monitor the output data generated from the UVC monitor sensor (not shown) in FIG. 4A that may be used with the UV lamp 140 and the UV shutter 145 to monitor the UV dose applied to the bill. If the UVC power is detected to have dropped, the verification module may reject the currency bill 250. The bill may be sent to the rejection tray 55.

In some embodiments, where the barcode 275 may not be used for sterilization verification, the processor 170 may verify that the bill is contaminated when contamination of the bill causes slippage of the bill in the rollers 315 of the bill feed motor 150. The bill may be sent to the rejection tray 55.

The embodiments shown in the figures above are merely for conceptual and visual clarity and not by way of limitation of the embodiments disclosed herein. For example, any suitable light source for producing any suitable wavelength of light known to kill pathogens attached to a currency bill may be used to sterilize the bill.

In some embodiments, the bill may not need guides 305 but may be moved and held in position using any suitable feed mechanism, particularly when the detection module 35 and sterilization module 40 are integrated into a cash machine.

In some embodiments, any number of sensors in any suitable configuration from the plurality of sensors for detecting the properties of the currency bills and the contaminants thereon may be used.

In some embodiments, any of the modules shown in the bill sterilization apparatus 10 may be integrated into a cash machine, or any other apparatus that processes currency bills. The bill sterilization apparatus 10 may receive data regarding the at least one property of the bill and/or the at least one bill contaminant from sensors and/or circuitry in the cash machine itself, such as from the cash acceptor, for example. In that case, only the UV Dose rate Application Module 230 (e.g., software module executed by the processor 170) and the sterilization module 40 may be implemented into the cash machine and needed for this scenario.

In some embodiments, the tray selector 50 and/or the bill storage tray 60 and/or the bill rejection tray 55 may be part of the cash machine and not part of the bill sterilization apparatus 10 as shown in FIG. 1.

Figure 5:
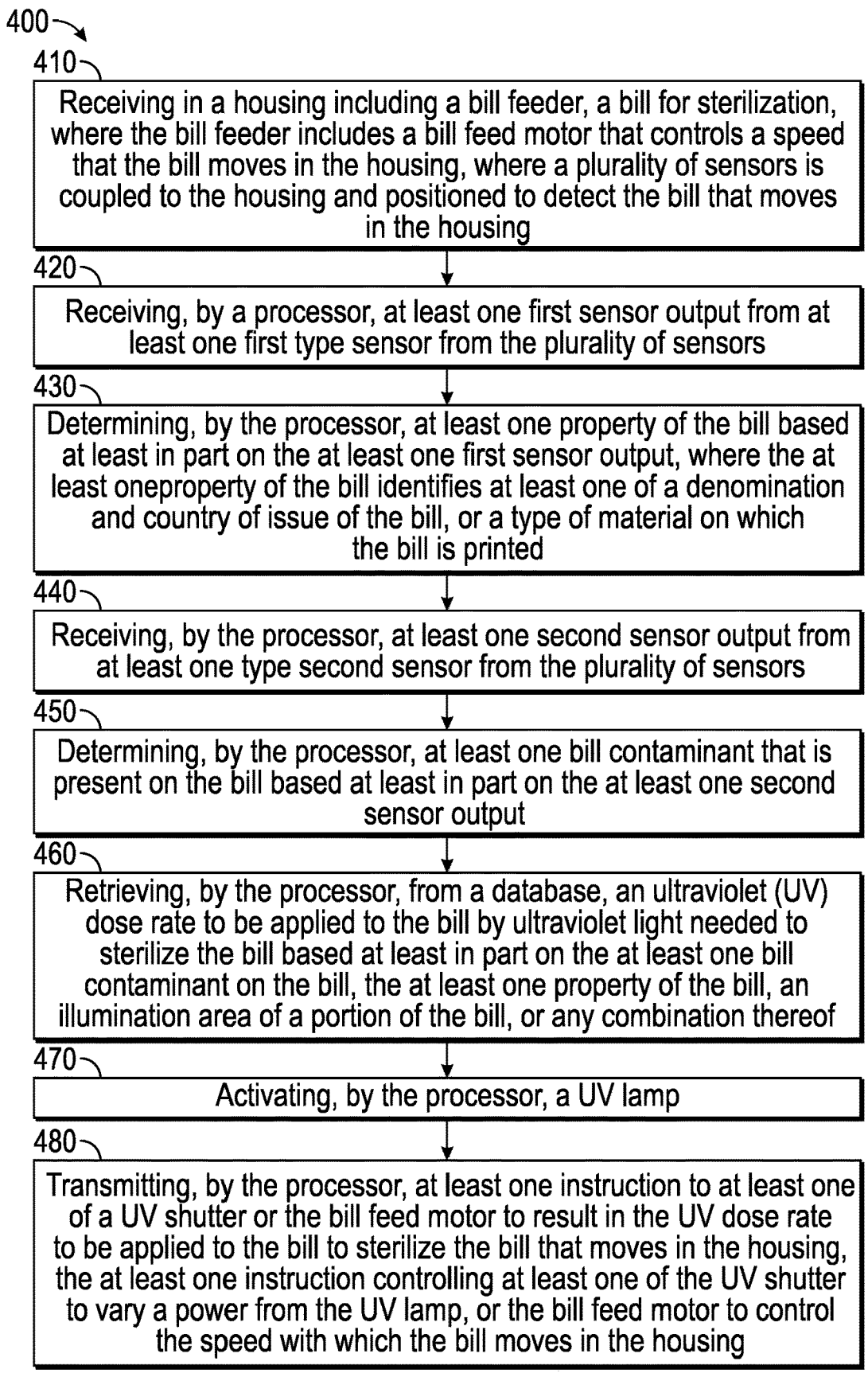
FIG. 5 is a flowchart of a method for sterilizing a bill in accordance with one or more embodiments of the present disclosure.

FIG. 5 is a flowchart of a method 400 for sterilizing a bill 250 in accordance with one or more embodiments of the present disclosure. The method 400 may be performed by the bill sterilization apparatus 10 and the processor 170.

The method 400 may include receiving 410 in a housing including a bill feeder, a bill for sterilization, where the bill feeder includes a bill feed motor that controls a speed that the bill moves in the housing, where a plurality of sensors is coupled to the housing and positioned to detect the bill that moves in the housing.

The method 400 may include receiving 420, by a processor, at least one first sensor output from at least one first type sensor from the plurality of sensors.

The method 400 may include determining 430, by the processor, at least one property of the bill based at least in part on the at least one first sensor output, where the at least one property of the bill identifies at least one of a denomination and country of issue of the bill, or a type of material on which the bill is printed.

The method 400 may include receiving 440, by the processor, at least one second sensor output from at least one second type sensor from the plurality of sensors.

The method 400 may include determining 450, by the processor, at least one bill contaminant that is present on the bill based at least on part on the at least one second sensor output.

The method 400 may include retrieving 460, by the processor, from a database, an ultraviolet (UV) dose rate to be applied to the bill by ultraviolet light needed to sterilize the bill based at least in part on the at least one bill contaminant present on the bill, the at least one property of the bill, an illumination area of a portion of the bill, or any combination thereof.

The method 400 may include activating 470, by the processor, a UV lamp.

The method 400 may include transmitting 480, by the processor, at least one instruction to at least one of a UV shutter or the bill feed motor to result in the UV dose rate to be applied to the bill to sterilize the bill that moves in the housing, the at least one instruction controlling at least one of the UV shutter to vary a power from the UV lamp, or the bill feed motor to control the speed with which the bill moves in the housing.

The material disclosed herein may be implemented in software or firmware or a combination of them or as instructions stored on a machine-readable medium, which may be read and executed by one or more processors such as processor 170. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others.

As used herein, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements of the bill sterilization apparatus 10 may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

In some embodiments, the I/O devices 210 may also comprise a number of external or internal devices such as a mouse, a CD-ROM, DVD, a physical or virtual keyboard, a display, a speaker, or other input or output devices.

Computer-related systems, computer systems, and systems, as used herein, include any combination of hardware and software. Examples of software may include software components, operating system software, middleware, firmware, software modules, routines, subroutines, functions, methods, procedures, software interfaces, application program interfaces (API), instruction sets, computer code, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that make the logic or processor. Of note, various embodiments described herein may, of course, be implemented using any appropriate hardware and/or computing software languages (e.g., C++, Objective-C, Swift, Java, JavaScript, Python, Perl, QT, etc.).

In some embodiments, one or more of exemplary inventive computer-based systems/platforms, exemplary inventive computer-based devices, and/or exemplary inventive computer-based components of the present disclosure, such as the controller 70, may include or be incorporated, partially or entirely into at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth, in addition to a cash machine.

In some embodiments, exemplary inventive computer-based systems/platforms, exemplary inventive computer-based devices, and/or exemplary inventive computer-based components of the present disclosure may be configured to utilize hardwired circuitry that may be used in place of or in combination with software instructions to implement features consistent with principles of the disclosure. Thus, implementations consistent with principles of the disclosure are not limited to any specific combination of hardware circuitry and software. For example, various embodiments may be embodied in many different ways as a software component such as, without limitation, a stand-alone software package, a combination of software packages, or it may be a software package incorporated as a "tool" in a larger software product.

For example, exemplary software specifically programmed in accordance with one or more principles of the present disclosure may be downloadable from a network, for example, a website, as a stand-alone product or as an add-in package for installation in an existing software application. For example, exemplary software specifically programmed in accordance with one or more principles of the present disclosure may also be available as a client-server software application, or as a web-enabled software application. For example, exemplary software specifically programmed in accordance with one or more principles of the present disclosure may also be embodied as a software package installed on a hardware device.

In some embodiments, the exemplary inventive computer-based systems/platforms, the exemplary inventive computer-based devices, and/or the exemplary inventive computer-based components of the present disclosure may be configured to securely store and/or transmit data by utilizing one or more of encryption techniques (e.g., private/public key pair, Triple Data Encryption Standard (3DES), block cipher algorithms (e.g., IDEA, RC2, RC5, CAST and Skipjack), cryptographic hash algorithms (e.g., MD5, RIPEMD-160, RTR0, SHA-1, SHA-2, Tiger (TTH), WHIRLPOOL, RNGs). The aforementioned examples are, of course, illustrative and not restrictive.

As used herein, the term "user" shall have a meaning of at least one user. In some embodiments, the terms "user", "subscriber" "consumer" or "customer" should be understood to refer to a user of an application or applications as described herein and/or a consumer of data supplied by a data provider. By way of example, and not limitation, the terms "user" or "subscriber" can refer to a person who receives data provided by the data or service provider over the Internet in a browser session, or can refer to an automated software application which receives the data and stores or processes the data.

At least some aspects of the present disclosure will now be described with reference to the following numbered clauses.

1. An apparatus may include:
    a housing for holding a bill and including a bill feeder;
        where the bill feeder may include a bill feed motor that controls a speed that the bill moves in the housing;
    a plurality of sensors coupled to the housing and positioned to detect the bill that moves in the housing;
    an ultraviolet (UV) lamp that emits ultraviolet light to illuminate a portion of the bill;
    a UV shutter to control a power of the ultraviolet light on the portion of the bill;
    a non-transitory computer memory; and
    a processor configured to execute computer code stored in the non-transitory computer memory that causes the processor to:
        receive at least one first sensor output from at least one first type sensor from the plurality of sensors;
        determine at least one property of the bill based at least in part on the at least one first sensor output;
            where the at least one property of the bill may identify at least one of:
            (i) a denomination and country of issue of the bill; or
            (ii) a type of material on which the bill is printed;
        receive at least one second sensor output from at least one second type sensor from the plurality of sensors;
        determine at least one bill contaminant that is present on the bill based at least in part on the at least one second sensor output;
        retrieve from a database a UV dose rate to be applied by the ultraviolet light needed to sterilize the bill based at least in part on:
            i) the at least one bill contaminant on the bill,
            ii) the at least one property of the bill,
            iii) an illumination area of the portion, or
            iv) any combination thereof;
        activate the UV lamp; and
        transmit at least one instruction to at least one of the UV shutter or the bill feed motor to result in the UV dose rate to be applied to the bill to sterilize the bill that moves in the housing, the at least one instruction controlling at least one of:
            (i) the UV shutter to vary the power from the UV lamp, or
            (ii) the bill feed motor to control the speed with which the bill moves in the housing.
2. The apparatus according to clause 1, where the at least one bill contaminant that is present on the bill may modify the UV dose rate of the bill relative to a nominal UV dose rate based only on the at least one property of the bill.
3. The apparatus as in any of clauses 1-2, where the processor may be configured to determine the at least one property of the bill from the at least one first sensor output of the at least one first type sensor by detecting features on the bill formed from the group consisting of magnetic ink, proportions of different inks, watermarks, Intaglio printing, a security thread, a see-through register, a special foil, special foil elements, an iridescent stripe, and shifting colors.
4. The apparatus as in any of clauses 1-3, where the at least one bill contaminant that is present on the bill may be selected from the group consisting of humidity, grease, skin oils, hand cream, glitter, and powder.
5. The apparatus as in any of clauses 1-4, further including a barcode reader, and where the barcode reader may be configured to read a barcode printed on the bill using a UV sensitive ink that becomes visible when the bill receives the UV dose rate needed to sterilize the bill.
6. The apparatus according to clause 5, where the processor may be further configured to verify that the bill is sterilized from an output of the barcode reader when the barcode is visible.
7. The apparatus according to clause 5, where the processor may be further configured to verify that the bill is contaminated from an output of the barcode reader when the barcode is invisible.
8. The apparatus as in any of clauses 1-7, where the at least one first type sensor may be a magnetic sensor, and where the processor may be configured to determine the at least one property of the bill from an output of the magnetic sensor that senses magnetic ink used to print the bill.
9. The apparatus as in any of clauses 1-8, where the ultraviolet lamp may emit the ultraviolet light at a UVC frequency.
10. The apparatus as in any of clauses 1-9, further including a bill storage tray for storing sterilized bills; where the processor may be configured to verify that the bill is sterilized and to cause a tray selector to route the bill in the housing into the bill storage tray.
11. The apparatus as in any of clauses 1-10, further including a bill rejection tray for storing contaminated bills; where the processor may be configured to verify that the bill is contaminated and to cause a tray selector in the housing to route the bill in the housing into the bill rejection tray.
12. The apparatus according to clause 11, where the processor may be configured to verify that the bill is contaminated when contamination of the bill causes slippage of the bill in rollers of the bill feed motor.
13. The apparatus as in any of clauses 1-12, where the at least one second type sensor may be a reflectometer, and where the processor may be configured to determine the at least one bill contaminant that is present on the bill from an output of the reflectometer.
14. A method may include:
    receiving in a housing including a bill feeder, a bill for sterilization;
    where the bill feeder may include a bill feed motor that controls a speed that the bill moves in the housing;
    where a plurality of sensors may be coupled to the housing and positioned to detect the bill that moves in the housing;
    receiving, by a processor, at least one first sensor output from at least one first type sensor from the plurality of sensors;
    determining, by the processor, at least one property of the bill based at least in part on the at least one first sensor output;
    where the at least one property of the bill may identify at least one of:
    (i) a denomination and country of issue of the bill; or
    (ii) a type of material on which the bill is printed;
    receiving, by the processor, at least one second sensor output from at least one second type sensor from the plurality of sensors;
    determining, by the processor, at least one bill contaminant that is present on the bill based at least in part on the at least one second sensor output;
    retrieving, by the processor, an ultraviolet (UV) dose rate to be applied to the bill by ultraviolet light needed to sterilize the bill based at least in part on:
    (i) the at least one bill contaminant on the bill,
    (ii) the at least one property of the bill,
    (iii) an illumination area of a portion of the bill, or
    (iv) any combination thereof;
    activating, by the processor, a UV lamp; and
    transmitting, by the processor, at least one instruction to at least one of the UV shutter or the bill feed motor to result in the UV dose rate to be applied to the bill to sterilize the bill that moves in the housing, the at least one instruction controlling at least one of:
    (i) the UV shutter to vary a power from the UV lamp, or
    (ii) the bill feed motor to control the speed with which the bill moves in the housing.
15. The method according to clause 14, where the ultraviolet lamp may emit the ultraviolet light at a UVC frequency.
16. The method as in any of clauses 14-15, where the at least one bill contaminant that is present on the bill may modify the UV dose rate of the bill relative to a nominal UV dose rate based only on the at least one property of the bill.
17. The method as in any of clauses 14-16, where the determining the at least one property of the bill from the at least one first sensor output of the at least one first type sensor may include detecting features on the bill formed from the group consisting of magnetic ink, proportions of different inks, watermarks, Intaglio printing, a security thread, a see-through register, a special foil, special foil elements, an iridescent stripe, and shifting colors.
18. The method as in any of clauses 14-17, where the at least one bill contaminant that is present on the bill may be selected from the group consisting of humidity, grease, skin oils, hand cream, glitter, and powder.
19. The method as in any of clauses 14-18, further including verifying, by the processor, that the bill is sterilized from an output of a barcode reader when a barcode printed on the bill using a UV sensitive ink is visible.
20. The method as in any of clauses 14-19, further including verifying, by the processor, that the bill is contaminated from an output of a barcode reader when a barcode printed on the bill using a UV sensitive ink is invisible.

Publications cited throughout this document are hereby incorporated by reference in their entirety. While one or more embodiments of the present disclosure have been described, it is understood that these embodiments are illustrative only, and not restrictive, and that many modifications may become apparent to those of ordinary skill in the art, including that various embodiments of the inventive methodologies, the inventive systems/platforms, and the inventive devices described herein can be utilized in any combination with each other. Further still, the various steps may be carried out in any desired order (and any desired steps may be added and/or any desired steps may be eliminated).

The invention claimed is:

1. An apparatus, comprising:
   a housing for holding a bill and comprising a bill feeder that controls the bill moving in the housing;
   an ultraviolet (UV) lamp that emits ultraviolet light to illuminate a portion of the bill;
   a UV shutter to control a power of the ultraviolet light on the portion of the bill;
   a non-transitory computer memory; and
   a processor configured to execute computer code stored in the non-transitory computer memory that causes the processor to:
      determine, from at least one sensor output of at least one sensor, at least one property of the bill;
      activate the UV lamp; and
      transmit at least one instruction to at least one of the UV shutter, the bill feeder, or both, so as to apply to the bill as the bill moves in the housing, a UV dose rate based at least in part on the at least one property of the bill.

2. The apparatus according to claim 1, wherein the bill comprises at least one bill contaminant that is present on the bill which modifies the UV dose rate of the bill relative to a nominal UV dose rate based only on the at least one property of the bill.

3. The apparatus according to claim 2, wherein the at least one bill contaminant that is present on the bill is selected from the group consisting of humidity, grease, skin oils, hand cream, glitter, and powder.

4. The apparatus according to claim 1, wherein the processor is configured to determine the at least one property of the bill from the at least one sensor output by detecting features on the bill formed from the group consisting of magnetic ink, proportions of different inks, watermarks, Intaglio printing, a security thread, a see-through register, a special foil, special foil elements, an iridescent stripe, and shifting colors.

5. The apparatus according to claim 1, further comprising a barcode reader, and wherein the barcode reader is configured to read a barcode printed on the bill using a UV sensitive ink that becomes visible when the bill receives the UV dose rate needed to sterilize the bill.

6. The apparatus according to claim 5, wherein the processor is further configured to verify that the bill is sterilized from an output of the barcode reader when the barcode is visible.

7. The apparatus according to claim 5, wherein the processor is further configured to verify that the bill is contaminated from an output of the barcode reader when the barcode is invisible.

8. The apparatus according to claim 1, wherein the at least one sensor is a magnetic sensor, and wherein the processor is configured to determine the at least one property of the bill from an output of the magnetic sensor that senses magnetic ink used to print the bill.

9. The apparatus according to claim 1, wherein the UV lamp emits the ultraviolet light at a UVC frequency.

10. The apparatus according to claim 1, further comprising a bill storage tray for storing sterilized bills; wherein the processor is configured to verify that the bill is sterilized and to cause a tray selector to route the bill in the housing into the bill storage tray.

11. The apparatus according to claim 1, further comprising a bill rejection tray for storing contaminated bills; wherein the processor is configured to verify that the bill is contaminated and to cause a tray selector from the bill feeder in the housing to route the bill in the housing into the bill rejection tray.

12. The apparatus according to claim 11, wherein the processor is configured to verify that the bill is contaminated when contamination of the bill causes slippage of the bill in rollers of a bill feed motor.

13. The apparatus according to claim 1, wherein the at least one sensor is a reflectometer, and wherein the processor is configured to determine at least one bill contaminant that is present on the bill from an output of the reflectometer.

14. A method, comprising:
   determining, by a processor, from at least one sensor output of at least one sensor: at least one property of a bill held in a housing comprising a bill feeder that controls the bill moving in the housing;
   activating, by the processor, a UV lamp that emits ultraviolet light to illuminate a portion of the bill; and
   transmitting, by the processor, at least one instruction to at least one of:
      a UV shutter that controls a power of the ultraviolet light on the portion of the bill,
      the bill feeder,
      or both,
      so as to apply to the bill as the bill moves in the housing, a UV dose rate based at least in part on the at least one property of the bill.

15. The method according to claim 14, wherein the UV lamp emits the ultraviolet light at a UVC frequency.

16. The method according to claim 14, wherein the bill comprises at least one bill contaminant that is present on the bill which modifies the UV dose rate of the bill relative to a nominal UV dose rate based only on the at least one property of the bill.

17. The method according to claim 16, wherein the at least one bill contaminant that is present on the bill is selected from the group consisting of humidity, grease, skin oils, hand cream, glitter, and powder.

18. The method according to claim 14, wherein the determining the at least one property of the bill from the at least one sensor output comprises detecting features on the bill formed from the group consisting of magnetic ink, proportions of different inks, watermarks, Intaglio printing, a security thread, a see-through register, a special foil, special foil elements, an iridescent stripe, and shifting colors.

19. The method according to claim 14, further comprising verifying, by the processor, that the bill is sterilized from an output of a barcode reader when a barcode printed on the bill using a UV sensitive ink is visible.

20. The method according to claim 14, further comprising verifying, by the processor, that the bill is contaminated from an output of a barcode reader when a barcode printed on the bill using a UV sensitive ink is invisible.

* * * * *